(12) United States Patent
Gorl et al.

(10) Patent No.: US 6,329,449 B1
(45) Date of Patent: Dec. 11, 2001

(54) PULVERULENT RUBBER POWDERS COMPRISING MODIFIED FILLERS, PROCESSES FOR THEIR PREPARATION AND THEIR USE

(75) Inventors: Udo Gorl, Recklingshausen; Reinhard Stober, Hasselroth; Hartmut Lauer, Bad-Soden-Salmunster; Uwe Ernst, Marl, all of (DE)

(73) Assignee: PKU Pulverkautschuk Union GmbH, Marl (DE)

( * ) Notice: Subject to any disclaimer, the term of this patent is extended or adjusted under 35 U.S.C. 154(b) by 0 days.

(21) Appl. No.: 09/401,850

(22) Filed: Sep. 22, 1999

(30) Foreign Application Priority Data

Sep. 22, 1998 (DE) ............................................. 198 43 301

(51) Int. Cl.$^7$ ........................................................ C08J 3/07
(52) U.S. Cl. ........................... 523/343; 523/213; 524/446; 524/571; 524/572; 528/14
(58) Field of Search ...................................... 523/334, 213; 524/446, 571, 572; 528/14

(56) References Cited

U.S. PATENT DOCUMENTS

| | | | |
|---|---|---|---|
| 3,922,240 | * | 11/1975 | Berg et al. . |
| 3,945,978 | * | 3/1976 | Berg et al. . |
| 3,998,778 | * | 12/1976 | Berg et al. . |
| 4,065,426 | * | 12/1977 | Yamawaki et al. . |
| 4,073,755 | * | 2/1978 | Berg et al. . |
| 4,138,375 | * | 2/1979 | Berg et al. . |
| 4,250,082 | * | 2/1981 | Sommer et al. . |
| 4,375,497 | * | 3/1983 | Sandstrom . |
| 4,578,411 | * | 3/1986 | Budd et al. . |
| 4,757,101 | * | 7/1988 | Kleinert et al. . |
| 4,788,231 | | 11/1988 | Smigerski et al. . |
| 4,835,196 | * | 5/1989 | Mueller er al. . |
| 4,883,829 | * | 11/1989 | Smigerski et al. . |
| 4,912,151 | * | 3/1990 | Tappe . |
| 5,017,630 | * | 5/1991 | Raines et al. . |
| 5,780,531 | | 7/1998 | Scholl . |

FOREIGN PATENT DOCUMENTS

| | | |
|---|---|---|
| 3723213 A1 | 1/1989 | (DE) . |
| 40 13 005 A1 | 10/1991 | (DE) . |
| 198 16 972 A1 | * 11/1999 | (DE) . |
| 0 753 549 A2 | 1/1997 | (EP) . |

* cited by examiner

*Primary Examiner*—Robert Dawson
*Assistant Examiner*—Kuo-Liang Peng
(74) *Attorney, Agent, or Firm*—Pillsbury Winthrop LLP

(57) ABSTRACT

The invention relates to a process for the preparation of finely divided rubbers (rubber powders) by precipitation from aqueous mixtures, which comprise filler in the form of suspensions, water-soluble salts of a metal of groups IIa, IIb, IIIa and VIII of the periodic table of the elements arid a rubber latex (polymer latex), aqueous emulsions of a rubber or rubber solution, in which one or more organosilicon compound(s) containing at least one alkoxy group is or are dissolved or emulsified, optionally in the presence of a surface-active substance, in water, or the compounds mentioned are mixed directly, optionally with a surface-active substance, with an aqueous suspension of an oxidic or silicatic finely divided filler or a mixture of these fillers at a temperature of 10 to 60° C., preferably at room temperature, while stirring, the amount of this mixture envisaged for incoporation in the rubber, based on the filler content, in general being divided into two batches.

23 Claims, No Drawings

PULVERULENT RUBBER POWDERS COMPRISING MODIFIED FILLERS, PROCESSES FOR THEIR PREPARATION AND THEIR USE

CROSS-REFERENCE TO RELATED APPLICATION

This application claims priority to German Application DE 198 43 301.8, filed Sep. 22, 1998, which disclosure is incorporated herein by reference.

FIELD OF THE INVENTION

The invention relates to a process for the preparation of rubber powders comprising fillers modified with organosilicon compounds, and the powders thus prepared.

BACKGROUND INFORMATION

A large number of publications have appeared relating to the aim and purpose of the use of powdered rubbers and possible processes for their preparation.

The explanation for the interest in pulverulent rubbers can readily be found from the processing techniques of the rubber industry. There, rubber mixtures are prepared with a high expenditure of time, energy and personnel. The main reason for this is that the raw material rubber takes the form of balls, and the other constituents of the vulcanizable mixture must be incorporated.

Comminution of the balls and intimate mixing with fillers, mineral oil plasticizers and vulcanization auxiliaries takes place on mills in internal mixers in several process stages. Between the stages, the mixture is generally cooled on a batch off-line, deposited on pallets as rolled sheets and intermediately stored. The internal mixers or mills are followed by appropriate extruders or calendering processes.

Only a completely new processing technology can lead away from this very involved technique of rubber processing.

The use of free-flowing rubber powders has therefore been considered for some time, because of the possibility of being able to process rubber mixtures easily and quickly in the same way as thermoplastic powders.

DE-PS 2822 148 discloses a process for the preparation of a pulverulent, filler-containing rubber.

According to this patent specification, an aqueous filler emulsion is added to a rubber latex (e.g. natural rubber) a rubber solution (e. g. BR) or an aqueous emulsion of a synthetic rubber (e. g. SBR) and the desired rubber powder is precipitated out.

To avoid the particle size-dependent filler contents obtained by this process, patents have been applied for relating to variants, for example DE-PS 15 3723 213 and DE-PS 3723 214.

DE-PS 3723213, discloses a process which proceeds in two stages. In the first step, an amount of ≧50% of the filler is integrated into the rubber powder particles. In the second step, the remainder of the filler is absorbed on to the so-called rubber base particles. This can be regarded as a variant of powdering, since no bond is formed between the filler and rubber.

As E. T. *Italiaander* (Paper 151. Technische Tagung der Rubber Div der ACS [Technical Conference of the Rubber Div. of the ACS], Anaheim, Calif. May 6–9 , 1997 (GAK 6/1997 (50) 456–464) found, however, regardless of the great future predicted in the Delphi Report (Delphi Report "Künftige Herstellverfahren in der Gummiindustrie [Future Production Processes in the Rubber Industry]" Rubber Journal, vol. 154, no. 11, 20–(1972)) for pulverulent and granulated rubber, and despite numerous attempts undertaken by well-known polymer producers from the mid 1970's into the early 1980's to prepare pulverulent NBR, SBR-carbon black masterbatches and granulated NR, the standard delivery form of polymers has remained rubber balls.

One disadvantage of the known processes lies in the fact that a grinding operation is required in order to establish the particle diameter of the filler particles of 10 $\mu$m regarded as necessary for the quality of the end product. This not only results in a high expenditure of energy, but also causes damage to the filler structure, which, along with the active surface area, is an important characteristic parameter for the effectiveness in use in rubbers.

Another disadvantage is that the ease of handling of the products according to the prior art suffers due to the particles sticking to one another during storage.

A precipitation process in which suspensions of fillers modified with organosilicon compounds are prepared and stirred into the rubber emulsion is the subject of German Patent application P 198 16 972.8. The rubber powder is then precipitated out of this mixture.

SUMMARY OF THE INVENTION

It is an object of the present invention to provide a process with few process stages which yields a rubber powder which comprises modified fillers and can be advantageously employed.

The invention provides a process for the preparation of finely divided rubbers (rubber powders) by precipitation from aqueous mixtures. The rubber composition so obtained comprises filler in the form of suspensions, water-soluble salts of a metal of groups IIa, IIb, IIIa and VIII of the periodic table of the elements and a rubber latex, an aqueous emulsion of a rubber or a rubber solution, which is characterized in that a) one or more organosilicon compound(s) containing at least one alkoxy group is or are dissolved or emulsified, optionally in the presence of a surface-active substance, in water, or the compounds mentioned are mixed directly, optionally with a surface-active substance, with an aqueous suspension of an oxidic or silicatic finely divided filler or a mixture of these fillers at a temperature of 10 to 60 ° C., preferably at room temperature, while stirring, the amount of this mixture envisaged for incoporation in the rubber, based on the filler content, in general being divided into two batches, and b) a first batch is mixed with the polymer latex, the polymer emulsion or the polymer solution, the pH of this mixture is lowered to 6.0 to 4.5 with an acid, in particular a Lewis acid (first batch, first stage), c) the remaining content (second batch, splitting amount) is added with further lowering of the pH to 4.5 to 2.6, in particular to approximately 3.2 (second stage), so that the rubber in the mixture precipitates out together with the filler modified by organosilicon compound(s)

d) the solid which has precipitated out is separated off by means known in the art, e) the product is then preferably washed, in order to adjust the pH to a value of approx. 6 to 7 which is more compatible with the further processing, and f) the filler-containing rubber is dried.

Drying is advantageously carried out in a drier at a gas intake temperature of 140 to 160° C. and a gas discharge temperature of 50 to 70° C. The temperature of the product should not exceed 40 to 50 ° C.

The duration, which depends on the pH and the filler content, and the extent of the precipitating operation can easily be determined by a measurement series using routine experimentation.

In the case of powdered rubber with a high filler content ($\geq$80 parts of filler phr), 1 to 10 parts of this amount will in general be employed as the remaining content in the second stage in the precipitation of the powdered rubber.

If the powdered rubber comprises less than 80 parts of filler phr, for example only 50 parts phr in total, >10 to 20 parts of this amount is further introduced into the mixture in the form of a suspension before the conclusion of the precipitating operation.

The fillers are bonded into the outer particle region (margin region) of the rubber powders in this manner.

These contents of the filler are therefore not absorbed externally on to the individual rubber particles (see DE-PS 37 23213), but are integrated into the rubber surface.

This distribution of the filler and the nature of the bonding of the fillers in the rubber composition cause the high flowability of the powders according to the invention and prevent agglutination during storage of the powders, without these properties being lost due to mechanical stresses during conveying, silation etc.

Further fillers which are optionally employed are the carbon blacks known from the rubber industry, preferably in finely divided form (fluffy), which in general have an average particle diameter of 1 to 9 $\mu$m, preferably 1 to 8 $\mu$m, without mechanical treatment, before they are suspended.

This facilitates dispersion, so that aqueous suspensions with filler particles having an average particle diameter of significantly less than 10 $\mu$m are obtained without a high expenditure of energy. Precipitated silica can advantageously be employed in the form of a filter-cake which has been washed free from salts.

Possible metal salts are those which originate from elements of groups IIa, IIb, IIIa and VIII of the periodic table of the elements. This classification into groups corresponds to the old IUPAC recommendation (see Periodisches System der Elemente [Periodic Table of the Elements], Verlag Chemie, Weinheim, 1985). Typical representatives are magnesium chloride, zinc sulfate, aluminium chloride, aluminium sulfate, iron chloride, iron sulfate, cobalt nitrate and nickel sulfate, the salts of aluminium being preferred. Aluminium sulfate and other Lewis acids are particularly preferred.

The salts are employed in an amount of 0.1 to 6.5 parts by weight per 100 parts by weight of rubber. The metal salts prove to be particularly suitable for controlling the particle size of the precipitated products in the desired manner. Mineral acids, such as for example sulfuric acid, phosphoric acid and hydrochloric acid, are optionally additionally used to establish the desired pH, sulfuric acid being particularly preferred. However, it is also possible to employ carboxylic acids, such as for example formic and acetic acid.

The amount of acid depends on the nature and amount of the water-soluble metal salt, of the filler, of the organosilane employed, of the rubber and of the alkali metal silicate optionally present. It can easily be determined by preliminary experiments.

In a preferred embodiment of the process according to the invention, Up to parts by weight of silica (SiO$_2$) per 100 parts by weight of rubber, in the form of an alkali metal silicate solution, preferably as water-glass with an Na$_2$O:SiO$_2$O molar ratio of 2:1 to 1:4, are also additionally employed. The alkali metal silicate solution can be added to the rubber component and/or to the filler suspension. Addition to the rubber component is preferred, especially in the continuous procedure.

The process according to the invention is in general carried out as follows: A filler suspension is first prepared by dispersing a portion, preferably $\geq$50%, of the filler to be contained in the end product, together with the metal salt, the organosilane compound and optionally the alkali metal silicate solution, in water, optionally in the presence of an emulsifier. The total amount of water employed depends on the nature of the filler and the degree of breakdown. In general, the water-insoluble constituents of the suspension are about 4 to 15 percent by weight. This is not a strict limitation; the actual value can be either below or above this. The maximum content is limited by the ability of the suspension to be pumped.

The filler suspension thus prepared is then mixed intimately with the rubber latex, which optionally contains alkali metal silicate solution, or the aqueous emulsion, which optionally contains alkali metal silicate solution, of a rubber solution (first batch, first stage). Known stirrer units, such as for example propeller stirrers, are suitable for this.

After mixing, a pH in the range from 6.0 to 4.5 is first established with further stirring, by addition of an acid, preferably a Lewis acid, in particular Al$_2$(SO$_4$)$_3$. Rubber base particles with a constant filler and organosilane content are obtained in this step. The size of these base particles is controlled by the amount of metal salt chosen, in the range from 0.1 to 6.5 phr. The largest particle size is obtained with the lowest amount of metal salt.

The remaining content of the filler suspension (second batch, splitting amount) is added with further lowering of the pH to 4.5 to 2.6, in particular to approximately 3.2 (second stage), so that the rubber in the mixture precipitates out together with the filler modified by organosilicon compound (s).

The solids content of the latices employed is in general 20 to 25 wt. %. The solids content of the rubber solutions is in general 3 to 35 wt. %, and that of the rubber emulsions is in general 5 to 30 wt. %.

For working up of rubber powders with filler contents of $\geq$100 phr it is advantageous to lower the pH to 2.5 before the phase separation. An acid from the aforementioned group of acids can be expediently used for this.

The process according to the invention can be carried out both discontinuously and continuously.

The rubber powder which has precipitated out is advantageously separated off with the aid of a centrifuge and then dried to a residual water content of in general $\leq$1%, in particular in a fluidized bed drier.

The rubber powders according to the invention are prepared using one or more organosilicon compounds of the general formula

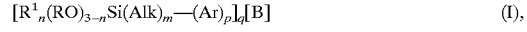 (I),

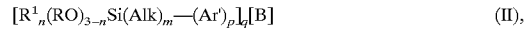 (II), or

 (III)

in which the symbols denote

B:—SCN, —SH, —Cl, —NH$_2$ (if q=1) or —S$_x$—(if q=2)

R and $R^1$: an alkyl group having 1 to 4 carbon atoms, branched or unbranched, the phenyl radical, where R and $R^1$ in each case can have the same or a different meaning, preferably an alkyl group, R: a $C_1$–$C_4$-alkyl, -$C_1$–$C_4$-alkoxy group, branched or unbranched, n: 0; 1 or 2, Alk: a divalent straight-chain or branched hydrocarbon radical having 1 to 6 carbon atoms, m: 0 or 1

Ar: an arylene radical having 6 to 12 carbon atoms p: 0 or 1, with the proviso that p and n do not simultaneously denote 0 x: a number from 2 to 8, alkyl: a straight-chain or branched unsaturated hydrocarbon radical having 1 to 20 carbon atoms, preferably 2 to 8 carbon atoms, alkenyl: a straight-chain or branched unsaturated hydrocarbon radical having 2 to 20 carbon atoms, preferably 2 to 8 carbon atoms.

These compounds, if they are water-soluble, are in general employed in the form of solutions, or otherwise in the form of emulsions, it also being possible for the emulsions to be formed in the presence of the silica suspension.

The emulsion or solution is preferably prepared at room temperature. However, temperatures of 10 to 60° C. are also suitable.

The concentration of the organosilicon compound(s) in the suspension is 0.5 to 20 wt. %, preferably 5 to 12 wt. %, based on the total amount of filler employed.

The pH of the emulsion or solution, like the pH of the filler suspension, after admixing of the emulsion is in the weakly acid or weakly alkaline range, but is preferably about 7.

The term "water-insoluble" is to be understood as follows:

After mixing the organosilane compound (without surface-active substance) with the suspension of the filler, no clear solution is formed around the filler particles in the desired pH and concentration range. Rather, the separate phases comprising water, solid and organosilicon compounds remain. The oligosulfidic organosilanes according to the general formula I given above are known in the art and can be prepared by known processes. Examples of organosilanes which are preferably employed are the bis (trialkoxysilyl-alkyl) oligosulfides which can be prepared for example in accordance with BE-PS 787 691, such as bis-(trimethoxy-, triethoxy-, -trimethoxy- ethoxy-, -tripropoxy-, -tributoxy-, -tri-i-propoxy- and -tri-i-butoxy- silyl-methyl) oligosulfides, and in particular the di-, tri-, tetra-, penta-, hexasulfides etc., furthermore bis-(2-trimethoxy-, -triathoxy-, -trimethoxyethoxy-, -tripropoxy- and -tri-n-and -i-butoxy-ethyl) oligosulfides and in particular the di-, tri-, tetra-, penta-, hexasulfides etc., and furthermore the bis-(3-trimethoxy-, -triethoxy-, -trimethoxyethoxy-, -tripropoxy-, -tri-n-butoxy- and tri-i-butoxysilyl-propyl) oligosulfides and in particular in turn the di-, tri-, tetrasulfides etc. up to octasulfides, and moreover the corresponding bis-(3-trialkoxysilylisobutyl) oligosulfides, the corresponding bis-(4-trialkoxysilylbutyl) oligosulfides. Of these selected organosilanes of the general formula I which are built up relatively simply, the bis-(3-trimethoxy-, -triethoxy- and tripropoxysilylpropyl) oligosulfides are in turn preferred, and in particular the di-, tri-, tetra- and pentasulfides, especially the triethoxy compounds with 2, 3 or 4 sulfur atoms, and mixtures thereof. Alk in the general formula I denotes a divalent, straight-chain or branched hydrocarbon radical, preferably a saturated alkylene radical with a straight carbon chain having 1 to 4 carbon atoms.

Compounds which are also specifically suitable are the silanes with the following structural formula

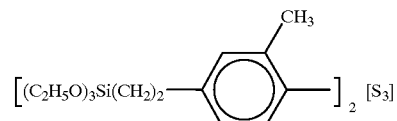

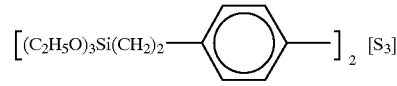

and methoxy analogues thereof, which can be prepared in accordance with DE-AS 25 58191. These compounds are not soluble in water.

Surface-active substances which are used in this case are, preferably, nonionic, cationic and anionic surfactants. Their concentration in the emulsion is 1 to 15 wt. %, preferably 2 to 10 wt. %, based on the amount of organosilane compounds.

Examples of such surfactants are alkylphenol polyglycol ethers, alkyl polyglycol ethers, polyglycols, alkyltrimethylammonium salts, dialkyldimethylammonium salts, alkylbenzyltrimethylammomium salts, alkylbenzenesulfonates, alkyl hydrogen sulfates, alkyl sulfates.

The naturally occurring or precipitated fillers to be modified, also as a mixture of two or more of these fillers, are fillers which are known in rubber technology. An essential prerequisite for their suitability is the presence of OH groups on the surface of the filler particles which can react with the alkoxy groups of the organosilicon compounds. These are oxidic and silicatic fillers which are compatible with rubbers and which have the fine division necessary and known for this use.

Kaolins or clays are particularly suitable as naturally occurring silicates. However, kieselguhr or diatomaceous earth can also be employed Examples of oxidic fillers which may be mentioned are aluminium oxide, aluminium hydroxide or trihydrate and titanium dioxide.

"Modified fillers" in this connection are those in which the organosilane compounds are bonded to the surface either by chemical reaction (OH groups) or adsorptively.

The adsorptively bonded groups are converted into chemically bonded groups by the drying step.

The emulsion is mixed with the filler suspension in amounts such that the concentration of the organosilicon compound is 0.5 to 20 wt. %, preferably 5 to 12 wt. %, based on the amount of filler. The modified fillers comprise 0.5 to 20 wt. %, preferably 0.5 to 12 wt. % of the organosilicon compounds, based on the dry filler.

They are particularly suitable for use in rubber mixtures which can be vulcanized and shaped.

A filter-cake from the silica precipitation which has been washed free from salts is advantageously employed for the process according to the invention. Suspensions such as those that are obtained by working up naturally occurring fillers, such as clays, are also suitable.

An energy-intensive drying step is thus saved, compared with the prior art.

The silicas employed are known from the rubber sector. In general, they have an $N_2$ surface area, determined by the known BET method, of 35 to 700 m²/g, a CTAB surface area of 30 to 500 m²/g, and a DBP number of 150 to 400 ml/100 g.

The product according to the invention comprises these silicas in an amount of 5 to 250 parts, in particular 20 to 100 parts, based on 100 parts of rubber.

If the fillers are white naturally occurring fillers, such as clays or siliceous chalks with an $N_2$ surface area of 2 to 35 m²/g, these are employed in an amount of 5 to 350 parts, based on 100 parts of rubber.

Filler-containing rubber powders which comprise silicas and carbon black as a mixture can also be prepared. However, the total amount of filler should not exceed 250 phr.

Carbon blacks such as those that are generally employed in rubber processing are particularly suitable.

These include furnace blacks, gas and flame blacks with an iodine adsorption number of 5 to 1000 m²/g, a CTAB number of 15 to 600 m²/g, a DBP adsorption of 30 to 400 ml/100 g and a 24 M4 DBP number of 50 to 370 ml/100 g, in an amount of 5 to 100 parts, in particular 20 to 100 parts per 100 parts of rubber.

It has been found possible to employ as rubber types and prepare as aqueous emulsions the following species, individually or as a mixture with one another: Natural rubber, emulsion SBR with a styrene content of 10 to 50%, butyl-acrylonitrile rubber. Butyl rubbers, terpolymers of ethylene, propylene (EPM) and non-conjugated dienes (EPDM), butadiene rubbers, SBR, prepared by the solution polymerization process, with styrene contents of 10 to 25%, and contents of 1,2-vinyl constituents of 20 to 55% and isoprene rubbers, in particular 3,4-polyisoprene.

In the case of polymers prepared by solvent processes, particular safety measures should be taken because of the solvent content.

In addition to the rubbers mentioned, the following elastomers are possible, individually or as a mixture: carboxyl rubbers, epoxide rubbers, transpolypentenamer, halogenated butyl rubbers, rubbers of 2-chloro-butadiene, ethylene/vinyl acetate copolymers, epichlorohydrins, optionally also chemically modified natural rubber, such as for example epoxidized types.

In addition to the fillers already mentioned, the rubber powders according to the invention optionally comprise known processing or vulcanization auxiliary substances, such as zinc oxide, zinc stearate, stearic acid, polyalcohols, polyamines, plasticizers, antioxidants against heat, light or oxygen and ozone, reinforcing resins, flameproofing agents, such as for example $Al(OH)_3$ and $Mg(OH)_2$, pigments, various crosslinking chemicals and optionally sulfur, in the conventional concentrations of rubber technology.

It is possible according to the invention to prepare a finely divided rubber powder which comprises silica modified with organosilicon compounds, is free-flowing and also remains free-flowing after exposure to mechanical stresses (e. g. conveying, packing). Because of its finely divided nature, no grinding or other comminution measures are necessary to obtain finely divided dispersions.

These then lead to the finely divided rubber powders which are easy to process, and to vulcanization products with improved properties.

References and patents cited herein are hereby incorporated by reference.

DETAILED DESCRIPTION OF THE INVENTION

The ease of implementation and the advantages of the present invention are explained in the following examples, without the invention being limited to these measures demonstrated.

| Raw materials used in the preparation | |
|---|---|
| E-SBR | Emulsion styrene-butadiene latex with a styrene content of 23.5% (BSL) |
| Si 69 | Bis(triethoxysilylpropyl)tetrasulfane (Degussa AG) |
| Si 75 | Bis(triethoxysilylpropyl)disulfane (Degussa AG) |
| Ultrasil VN3, Ultrasil VN3 filter-cake | Precipitated silica with an $N_2$ surface area (BET) of 175 m²/g (Degussa AG), dried or as a filter-cake, optionally granulated (gran) |
| Ultrasil 7000, Ultrasil 7000 filter-cake | Precipitated silica with an $N_2$ surface area (BET) of 175 m²/g and improved dispersing properties (Degussa AG), dried or as a filter-cake, optionally granulated (gran) |
| Marlipal 1618/25 | Emulsifier: fatty alcohol polyethylene glycol ether (Hüls AG) |

EXAMPLE 1
Preparation of Powdered Rubber Based on E-SBR, Ultrasil 7000 and Si 69

A stable suspension of 14.3 kg Ultrasil 7000, 1.58 kg Si 69 ( corresponds to 11.3%, based on the silica ), 142 g Marlipal 1618/25 (corresponds to 1% based on the silica ) in 255L water is prepared, while stirring, and is then apportioned in the ratio 5:1.

The larger portion of the suspension is mixed with 94.3 L of a 21.0% E-SBR latex emulsion, with vigorous stirring, and then lowered to a pH of 5.0 by addition of an approx. 10% $Al_2(SO_4)_3$ solution. This first precipitating step is followed by addition of the second portion of the suspension, prepared as above, with subsequent lowering of the pH to an end point of 3.7.

After the precipitating process, mechanical removal of most of the water takes place, followed by a drying step to a residual moisture content of <1% . The pulver-ulent finished product (EPB 1) comprises 100 parts E-SBR and 77 parts Ultrasil 7000/Si 69 ( 11.3% ), determined by means of thermogravimetric analysis (TGA).

EXAMPLE II
Preparation of Powdered Rubber Based on E-SBR, Ultrasil 7000 filter-cake and Si 69

A stable suspension of 59.0 kg Ultrasil 7000 filter-cake, 1.60 kg Si 69 (corresponds to 11.3%, based on the silica), 140 g Marlipal 1618/25 (corresponds to 1%, based on the silica) in 189L water is prepared, while stirring, and is then apportioned in the ratio 5:1.

The larger portion of the suspension is mixed with 95.7L of a 20.5% E-SBR latex emulsion, with vigorous stirring, and then lowered to a pH of 4.9 by addition of an approx. 10% $Al_2(SO_4)_3$ solution. This first precipitating step is followed by addition of the second portion of the suspension, prepared as above, with subsequent lowering of the pH to 3.4.

After the precipitating process, mechanical removal of most of the water takes place, followed by a drying step to a residual moisture content of <1% . The pulverulent finished product (EPB 2) comprises 100 parts E-SBR and 83 parts Ultrasil 7000 (from filter-cake)/Si 69 (11.3% ), (TGA determination).

EXAMPLE III
Preparation of Powdered Rubber Based on E-SBR, Ultrasil VN3 and Si 69

A stable suspension of 13.9 kg Ultrasil VN3, 1.55 kg Si 69 (corresponds to 11.3%, based on the silica), 137 g Marlipal 1618/15 (corresponds to 1%, based on the silica) in 267L water is prepared, while stirring, and is then apportioned in the ratio 5:1.

The larger portion of the suspension is mixed with 94.7 L of a 20.9% E-SBR latex emulsion, with vigorous stirring, and then lowered to a pH of 5.2 by addition of an approx. 10% $Al_2(SO_4)_3$ solution. This first precipitating step is followed by addition of the second portion of the suspension, prepared as above, with subsequent lowering of the pH to 3.5.

After the precipitating process, mechanical removal of most of the water takes place, followed by a drying step to a residual moisture content of <1%. The pulverulent finished product (EPB 3) comprises 100 parts E-SBR and 72 parts Ultrasil VN3/Si 69 (11.3%), (TGA determination).

EXAMPLE IV

Preparation of Powdered Rubber Based on E-SBR, Ultrasil 7000 and Si 75

A stable suspension of 14.6 kg Ultrasil 7000, 1.59 kg Si 75 (corresponds to 11.3%, based on the silica), 142 g Marlipal 1618/15 (corresponds to 1%, based on the silica) in 258L water is prepared, while stirring, and is then apportioned in the ratio 5:1.

The larger portion of the suspension is mixed with 93.8 L of a 21.5% E-SBR latex emulsion, with vigorous stirring, and then lowered to a pH of 5.11 by addition of an approx. 10% $Al_2(SO_4)_3$ solution. This first precipitating step is followed by addition of the second portion of the suspension (saturation agent) with subsequent lowering of the pH to 3.3.

After the precipitating process, mechanical removal of most of the water takes place, followed by a drying step to a residual moisture content of <%. The pulverulent finished product (EPB 4) comprises 100 parts E-SBR and 76 parts Ultrasil 7000/Si 75 (11.3%), (TGA determination).

EXAMPLE V

Preparation of Powdered Rubber Based on E-SBR, Ultrasil 7000 filter-cake Si 75

A stable suspension of 61.0 kg Ultrasil 7000 filter-cake, 1.63 kg Si 75 (corresponds to 11.3%, based on the silica), 140 g Marlipal 1618/25 (corresponds to 1%, based on the silica) in 1951 water is prepared, while stirring, and is then apportioned in the ratio 5:1.

The larger portion of the suspension is mixed with 96.2 L of a 20.5% E-SBR latex emulsion, with vigorous stirring, and then lowered to a pH of 4.8 by addition of an approx. 10% $Al_2(SO_4)_3$ solution. This first precipitating step is followed by addition of the second portion of the suspension (saturation agent) with subsequent lowering of the pH to 3.5.

After the precipitating process, mechanical removal of most of the water takes place, followed by a drying step to a residual moisture content of <1%. The pulverulent finished product (EPB 5) comprises 100 parts E-SBR and 80 parts Liltrasil 7000 (from filter-cake)/Si 75 (11.3%), (TGA determination).

The following products were employed in the rubber technology use:

| Chemicals | |
|---|---|
| SBR 1500 | Styrene-butadiene rubber with a styrene content of 23.5% |
| Naftolen ZD | Arom. mineral oil plasticizer |
| EPB 1 | Powdered rubber comprising 100 parts E-SBR 1500, 77 parts Ultrasil 7000/Si69 |
| EPB 2 | Powdered rubber comprising 100 parts E-SBR 1500, 83 parts Ultrasil 7000 (fromfilter-cake)/Si69 |
| EPB 3 | Powdered rubber comprising 100 parts E-SBR 1500, 72 parts Ultrasil VN3/Si69 |
| EPB 4 | Powdered rubber comprising 100 parts E-SBR 1500, 76 parts Ultrasil 7000/Si75 |
| EPB 5 | Powdered rubber comprising 100 parts E-SBR, 80 parts Ultrasil 7000 (from filter cake)/Si75 |
| 6 PPD | N-(1,3-Dimethylbuthyl)-N-phenyl-p-phenylenediamine [sic] |
| CBS | Benzothiazyl-2-cyclohexylsulfenamide |
| DPG | Diphenylguanidine |

The following test methods of rubber technology were used:

| | |
|---|---|
| Mooney viscosity | DIN 53 523/3 |
| Tensile test on bar | DIN 53 504 |
| Shore hardness | DIN 53 505 |
| Tear propagation resistance | ASTM D 624 |
| Abrasion | DIN 53 516 |
| Dispersion (Philips) | ISO/DIS 11 345 |
| Dispersion (coarseness) | DIN 4788 |
| Elongation at break | DIN 53504 |
| Breaking energy | DIN 53504 |

EXAMPLE A

Comparison of the Rubber Technology Profile of Values of the Product According to the Invention (Preparation Example 1) Against a Standard Mixture.

a) Recipe

| Mixture | 1 [phr] | 2 [phr] |
|---|---|---|
| SBR 1500 | 100 | — |
| EPB 1 | — | 177 |
| Ultrasil 7000 gran | 70 | — |
| Si 69 | 9 | — |
| Naftolen ZD | 25 | 25 |
| ZnO | 3 | 3 |
| Stearic acid | 2 | 2 |
| 6 PPD | 2 | 2 |
| Wax | 1 | 1 |
| CBS | 1.7 | 1.7 |
| DPG | 2 | 2 |
| Sulfur | 1.5 | 1.5 | b) Mixing process
1st stage

Internal mixer: GK 1.5 E; Volume 1.5 L; Friction 1:1;
Stamp 5.5 bar

| Mixture | 1 | 2 |
|---|---|---|
| Filling level | 0.55 | 0.6 |
| RPM | 50 | 40 |
| Flow temperature [° C.] | 60 | 60 |
| 0–0.5' SBR 1500 | 0–1' EPB 1, ZnO, stearic acid, oil, 6 PPD, | |
| 0.5–1' ½ Ultrasil 7000, ½ Si 69, oil, ZnO, | Wax | |

-continued b) Mixing process
1st stage

| stearic acid, wax | 1–4' mix and eject |
|---|---|
| 1–2' ½ Ultrasil 7000, ½ Si 69, 6 PPD | |
| 2' clean | |
| 2–4' mix and eject | |
| Ejection temperature ~135° C. | Ejection temperature ~135° C. |

2nd stage

Internal mixer: GK 1.5 E; Volume 1.5 L; Friction 1:1;
Stamp 5.5 bar; RPM 30; Filling level 0.53;
Flow temperature 60° C.
Both mixtures
0–1,5' Batch stage 1, accelerator, sulfur
1.5' Ejection and pull out rolled sheet c) Rubber technology data

| Mixture number | 1 | 2 |
|---|---|---|
| ML 1 + 4 | 45 | 51 |
| Tensile strength [MPa] | 21.4 | 25.0 |
| Elongation at break [%] | 450 | 600 |
| Breaking energy [J] | 20.3 | 30.8 |
| Shore A hardness | 71 | 69 |
| Tear propagation resistance ASTM DIE C [N/mm] | 50 | 57 |
| Abrasion [mm$^3$] | 82 | 69 |
| Dispersion (Philips) | 7 | 8 |
| Dispersion (coarseness) | 613 | 36 |
| Coarseness factor Pc$^2$ Pa | | |

The powdered rubber from E-SBR latex, Ultrasil 7000 and Si 69 is distinguished by higher strength values, a more favourable abrasion and a significantly improved dispersion compared with the conventional mixing procedure.

EXAMPLE B

Comparison of the rubber technology profile of values of the product according to the invention EPB 2 (E-SBR/Ultrasil VN3/Si69), EPB 3 (E-SBR/Ultrasil VN3 filter-cake/Si69)

a) Recipe

| Mixture | 1 [phr] | 2 [phr] |
|---|---|---|
| EPB 2 | 172 | — |
| EPB 3 | — | 172 |
| Naftolen ZD | 25 | 25 |
| ZnO | 3 | 3 |
| Stearic acid | 2 | 2 |
| 6 PPD | 2 | 2 |
| Wax | 1 | 1 |
| CBS | 1.7 | 1.7 |
| DPG | 2 | 2 |
| Sulfur | 2.2 | 2. | b) Mixing process
1st stage

Internal mixer: GK 1.5 E; Volume 1.5 L; Friction 1:1;
Stamp 5.5 bar

| Mixture | 1.2 |
|---|---|
| Filling level | 0.6 |
| RPM | 40 |
| Flow temperature [° C.] | 600 |

0–1' EPB 2 or EPB 3,
ZnO, stearic acid, oil,
6 PPD, wax
1–4' mix and eject
Ejection temperature ~135° C.

2. stage

Internal mixer: GK 1.5 E; Volume 1.5 L; Friction 1:1;
Stamp 5.5 bar; RPM 30; Filling level 0.53;
Flow temperature 60° C.
Both mixtures
0–1,5' Batch stage 1, accelerator, sulfur
1.5' Ejection and pull out rolled sheet c) Rubber technology data

| Mixture number | 1 | 2 |
|---|---|---|
| ML 1 + 4 | 51 | 56 |
| Tensile strength [MPa] | 19.7 | 21.0 |
| 300% modulus {MPa} | 6.4 | 6.4 |
| Elongation at break [%] | 630 | 650 |
| Breaking energy [J] | 163 | 180 |
| Shore hardness | 67 | 69 |
| Din abrasion [mm$^3$] | 99 | 88 |
| Dispersion (Philips) | 5 | 8 |
| Dispersion (coarseness) | 3000 | 108 |
| Coarseness factor Pc$^2$ Pa | | |

The powdered rubber from E-SBR latex, Ultrasil VN3 filter-cake and Si 69 (EPB 3) is distinguished by higher strength values, a better abrasion and by an excellent dispersion in the compound compared with Ultrasil VN 3 (EPD 2)

EXAMPLE C

Comparison between EPB 4 (E-SBR/Ultrasil VN3 filter-cake Si69) and EPB 5 (E-SBR/Ultrasil 7000 filter-cake/Si69)

a) Recipe

| Mixture | 1 [phr] | 2 [phr] |
|---|---|---|
| EPB 4 | 176 | — |
| EPB 5 | — | 180 |
| Naftolen ZD | 25 | 25 |
| ZnO RS | 3 | 3 |
| Stearic acid | 2 | 2 |
| 6 PPD | 2 | 2 |
| Wax | 1 | 1 | a) Recipe

| | | |
|---|---|---|
| CBS | 1.7 | 1.7 |
| DPG | 2 | 2 |
| Sulfur | 1.5 | 1.5 | b) Mixing process
1st stage

Internal mixer: GK 1.5 E; Volume 1.5 L; Friction 1:1;
Stamp 5.5 bar

| | |
|---|---|
| Mixture | 1.2 |
| Filling level | 0.6 |
| RPM | 40 |
| Flow temperature [° C.] | 60 |

0–1' EPB 4 or EPB 5,
ZnO, stearic acid, oil,
6 PPD, wax
1–4' mix and
eject
Ejection temperature ~135° C.

2nd stage

Internal mixer: GK 1.5 E; Volume 1.5 L; Friction 1:1;
Stamp 5.5 bar; RPM 30; Filling level 0.53;
Flow temperature 60° C.
Both mixtures
0–1.5' Batch stage 1, accelerator, sulfur
1.5' Ejection and pull out rolled sheet c) Rubber technology data

| Mixture number | 1 | 2 |
|---|---|---|
| Tensile strength [MPa] | 18.2 | 20.3 |
| 300% modulus {MPa} | 6.7 | 8.9 |
| Breaking energy [J] | 138 | 149 |
| Shore hardness | 70 | 72 |
| DIN abrasion [mm³] | 97 | 81 |
| Dispersion (Philips) | 8 | 9 |
| Dispersion (coarseness) | 90 | 16 |
| Coarseness factor Pc² Pa | | |

The product EPB 5 with Ultrasil 7000 filter-cake/Si 75 is distinguished by even better strength values, a further increase in the abrasion resistance and a better dispersion compared with the Ultrasil VN3 filter-cake (EPB 4).

What is claimed is:

1. A process for the preparation of finely divided rubbers (rubber powders) by precipitation from aqueous mixtures which comprise filler in the form of suspensions, water-soluble salts of a metal of groups IIa, IIb, IIIa and VIII of the periodic table of the elements and a rubber latex (polymer latex), aqueous emulsions of a rubber or rubber solution, comprising a) dissolving or emulsifying one or more organosilicon compound(s) containing at least one alkoxy group in water, optionally in the presence of a surface-active substance, with an aqueous suspension of an oxidic or silicatic finely divided filler or a mixture of these fillers at a temperature of 10 to 60° C., while stirring, and appoitioning an amount of this mixture to be incorporated in the rubber, based on the filler content, into a first batch and a second batch;

b) mixing the first batch with the polymer latex, the polymer emulsion or the polymer solution and lowering the pH of the resulting mixture to 6.0 to 4.5 with an acid (first batch, first stage);

c) adding the second batch to said mixture (second batch, splitting amount) and lowering of the pH to 4.5 to 2.6 (second stage), so that the rubber in the mixture precipitates out together with the filler modified by organosilicon compound(s) as a solid;

d) separating the solid which has precipitated out from the mixture;

e) optionally washing said solid to adjust the pH to a value of 6 to 7; and f) drying the filler-containing rubber.

2. The process according to claim 1 wherein step a) is carried out at room temperature.

3. The process according to claim 1 wherein the acid of step b) is a Lewis acid.

4. The process according to claim 1 wherein the pH is lowered to approximately 3.2 in step c).

5. The process according to claim 1 wherein one or more organosilicon compounds are of formula $$[R^1{}_n(RO)_{3-n}Si\text{-}(Alk)_m\text{-}(Ar)_p]_q[B] \qquad (I),$$

$$R^1{}_n(RO)_{3-n}Si\text{-}(alkyl) \qquad (II),$$

or $$R^1{}_n(RO)_{3-n}Si\text{-}(alkenyl) \qquad (III)$$

in which the symbols denote

B: —SCN, —SH, —Cl, —NH₂ (if q=1) or —Sx—(if q=2),

R and R¹: a branched or unbranched alkyl group having 1 to 4 carbon atoms or a phenyl radical, wherein R and R¹ in each case may be the same or different, R: a branched or unbranched C₁–C₄-alkyl or C₁–C₄-alkoxy group, n: 0, 1 or 2, Alk: a divalent straight-chain or branched hydrocarbon radical having 1 to 6 carbon atoms, m: 0 or 1, Ar: an arylene radical having 6 to 12 carbon atoms, p: 0 or 1, with the proviso that p and n do not simultaneously denote 0, x:. a number from 2 to 8, alkyl: a straight-chain or branched unsaturated hydrocarbon radical having 1 to 20 carbon atoms, alkenyl: a straight-chain or branched unsaturated hydrocarbon radical having 2 to 20 carbon atoms.

6. The process according to claim 5 which includes at least one compound wherein R or R¹ is an alkyl group.

7. The process according to claim 5 which includes at least one organosilicon compound of formula (III) wherein the alkenyl group contains 2 to 8 carbon atoms.

8. The process according to claim 1 wherein nonionic, cationic or anionic surfactants are employed as the surface-active substances.

9. The process according to claim 8, wherein the surfactants are employed in an amount of 1 to 15 wt. % based on the amount of organosilane compounds in the emulsion.

10. The process according to claim 8, wherein the surfactants are employed in an amount of 2 to 10 wt. %, based on the amount of organosilane compounds in the emulsion.

11. The process according to claim 8, wherein a surfactant from the class of fatty alcohol polyethylene glycol ethers or alkylphenol polyethylene glycol ethers is employed.

12. The process according to claim 1 wherein the concentration of the organosilicon compound in the suspension 0.5 to 12 wt. %, based on the filler (absolutely dried).

13. The process according to claim 1 wherein the rubber powder is precipitated in the presence of an acid.

14. The process according to claim 13 wherein the acid is a lewis acid.

15. The process according to claim 13 wherein the acid is $Al_2(SO_4)_3$.

16. The process according claim 1, wherein the filter-cake of a precipitated silica, washed free from salts, is employed in particular as the filler in stage a).

17. The process according to claim 1 wherein a solid obtained by working up naturally occuring fillers is employed.

18. The process according to claim 1 wherein $\geq 50$ parts of the filler content of the rubber powder product is added in step b).

19. The process according to claim 1 wherein at a content of $\geq 80$ parts of filler phr (per hundred parts of rubber), 90 to 99% of the filler content of the rubber powder product is added in step b).

20. The process according to claim 1 wherein a carbon black which can be employed in rubber technology is added in the desired amount to the emulsion/suspension according to step a) or the mixture according to step b).

21. The process according to claim 1 wherein conventional processing auxiliary substances, antioxidants, activators and/or crosslinking chemicals of rubber technology and sulfur are added in the conventional amounts either to the emulsion, suspension or solution according to claim 1, step a) or to the mixtures produced according to steps b) and c).

22. The process according to claim 5 wherein the alkyl has 2 to 8 carbon atoms.

23. The process according to claim 17, wherein the naturally occurring fillers include clay.

* * * * *